(12) United States Patent
Ohirabaru et al.

(10) Patent No.: US 9,841,279 B2
(45) Date of Patent: Dec. 12, 2017

(54) APPARATUS AND METHOD FOR QUANTITATIVE EVALUATION OF BRAZE BONDING LENGTH WITH USE OF RADIATION

(71) Applicant: Kabushiki Kaisha Toshiba, Minato-ku (JP)

(72) Inventors: Ryosuke Ohirabaru, Yokohama (JP); Makoto Takanezawa, Yokohama (JP); Kazuya Segawa, Yokohama (JP); Hideyuki Nakamura, Tokyo (JP); Shigeru Harada, Hino (JP); Fumio Sato, Yokohama (JP); Satoru Asai, Chigasaki (JP); Akio Sumita, Yokohama (JP); Tooru Ootaka, Kawasaki (JP)

(73) Assignee: KABUSHIKI KAISHA TOSHIBA, Minato-ku (JP)

(*) Notice: Subject to any disclaimer, the term of this patent is extended or adjusted under 35 U.S.C. 154(b) by 128 days.

(21) Appl. No.: 15/066,121

(22) Filed: Mar. 10, 2016

(65) Prior Publication Data

US 2016/0265909 A1  Sep. 15, 2016

(30) Foreign Application Priority Data

Mar. 10, 2015 (JP) ................................ 2015-047639

(51) Int. Cl.
*G01B 15/00* (2006.01)
*G01N 23/04* (2006.01)
(Continued)

(52) U.S. Cl.
CPC ............ *G01B 15/025* (2013.01); *G01B 15/00* (2013.01); *G01N 23/043* (2013.01); *G01N 23/06* (2013.01); *G21K 1/02* (2013.01)

(58) Field of Classification Search
CPC ..... G01B 15/00; G01B 15/025; G01N 23/043; G01N 23/06
See application file for complete search history.

(56) References Cited

U.S. PATENT DOCUMENTS 5,561,696 A    10/1996  Adams et al.
5,933,473 A     8/1999  Kitaguchi et al.
(Continued)

FOREIGN PATENT DOCUMENTS

JP    2001-241932         9/2001
JP    2008-256603 A      10/2008
(Continued)

OTHER PUBLICATIONS

Extended European Search Report dated Aug. 12, 2016 in Patent Application No. 16157872.9.

*Primary Examiner* — Mark R Gaworecki
(74) *Attorney, Agent, or Firm* — Oblon, McClelland, Maier & Neustadt, L.L.P.

(57) ABSTRACT

According to an embodiment, there is provided an apparatus which quantitatively evaluates a braze bonding length. A radiation emission unit emits radiation to each of a plurality of partial specimens which are obtained by cutting a specimen in a plane perpendicular to a braze bonding length direction. A light generator generates light of an amount corresponding to an intensity of transmissive radiation. An imaging unit photographs this light. A calculator calculates a braze bonding length of each of the partial specimens, from a light amount obtained with respect to each of the partial specimens, based on a correlation between a braze bonding length and a light amount. The calculator further calculates the braze bonding length of the specimen by totaling the braze bonding lengths of the respective partial specimens.

16 Claims, 15 Drawing Sheets

(51) Int. Cl.
*G01N 23/06* (2006.01)
*G01B 15/02* (2006.01)
*G21K 1/02* (2006.01)

(56) References Cited

U.S. PATENT DOCUMENTS

| | | |
|---|---|---|
| 6,049,586 A | 4/2000 | Kitaguchi et al. |
| 6,333,962 B1 | 12/2001 | Kitaguchi et al. |
| 2001/0053197 A1 | 12/2001 | Murayama et al. |
| 2010/0119037 A1 | 5/2010 | Kato et al. |

FOREIGN PATENT DOCUMENTS

| | | |
|---|---|---|
| JP | 2009-198463 | 9/2009 |
| JP | 4444729 | 3/2010 |
| JP | 2014-106113 | 6/2014 |
| KR | 10-2010-0044680 A | 4/2010 |

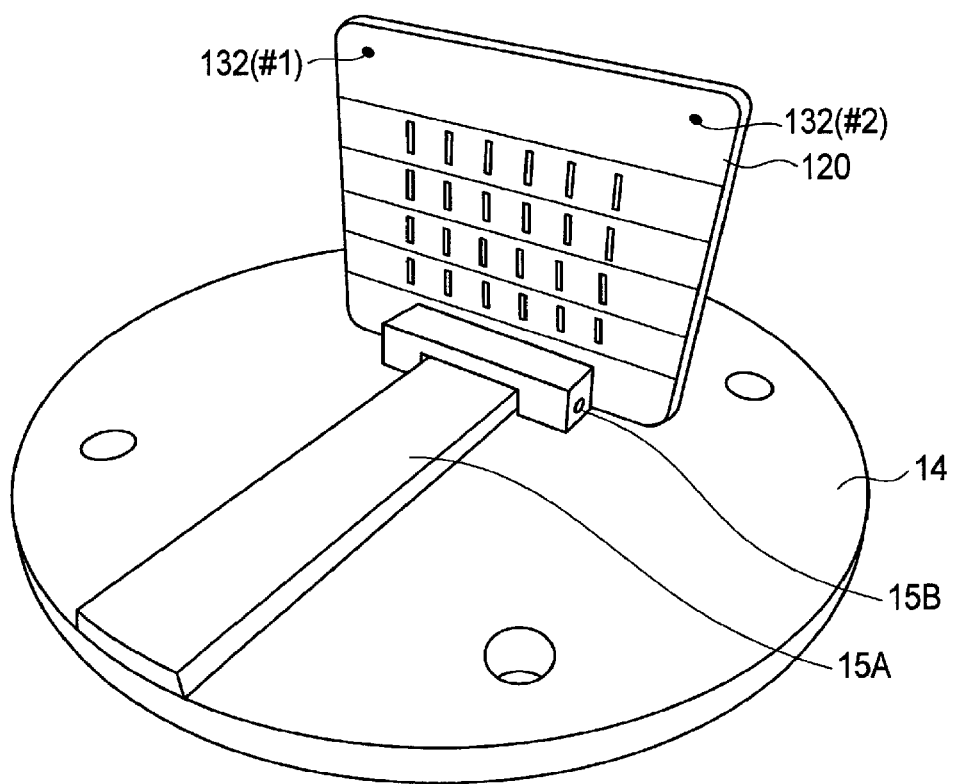
F I G. 3

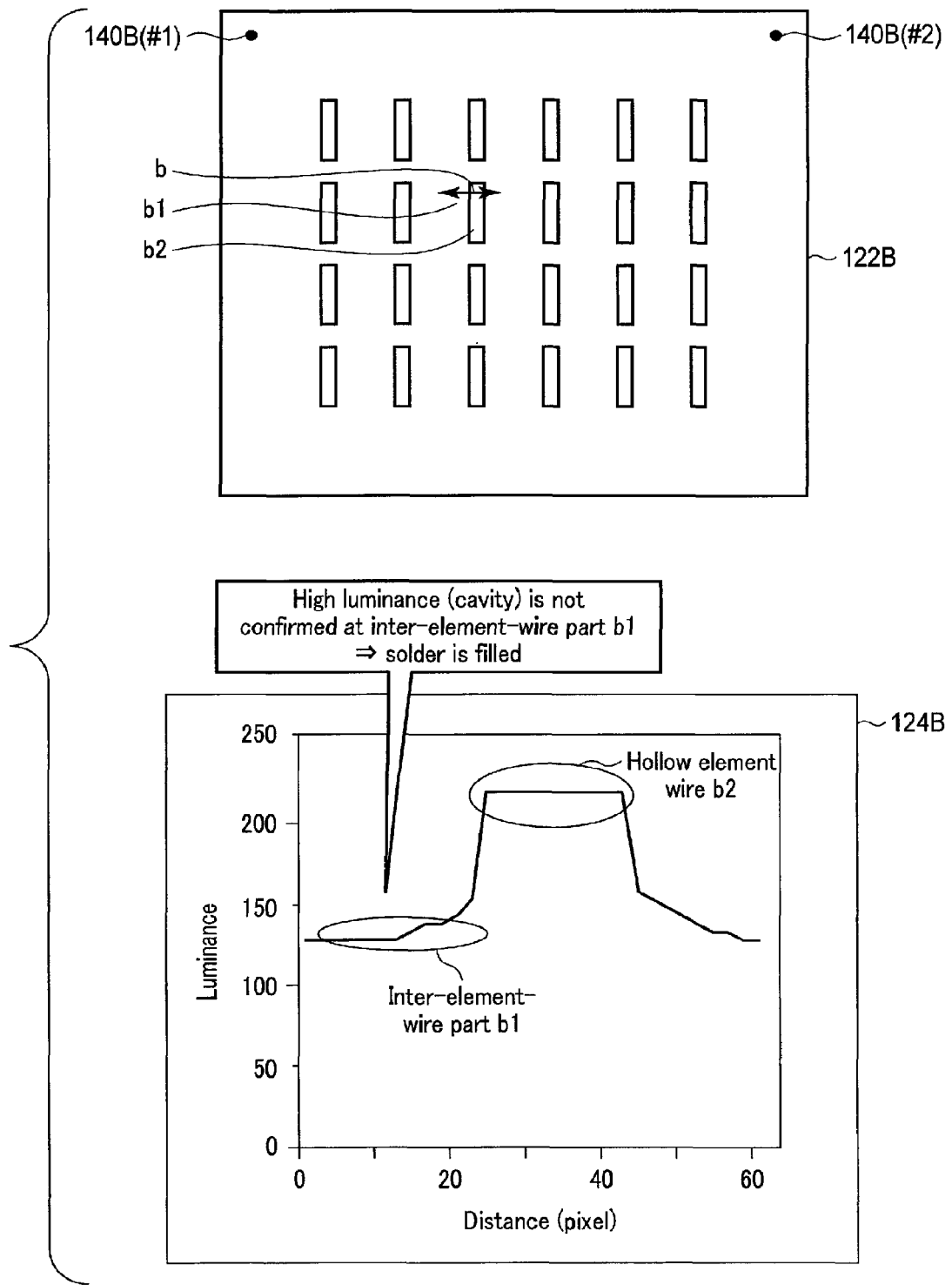
F I G. 4B

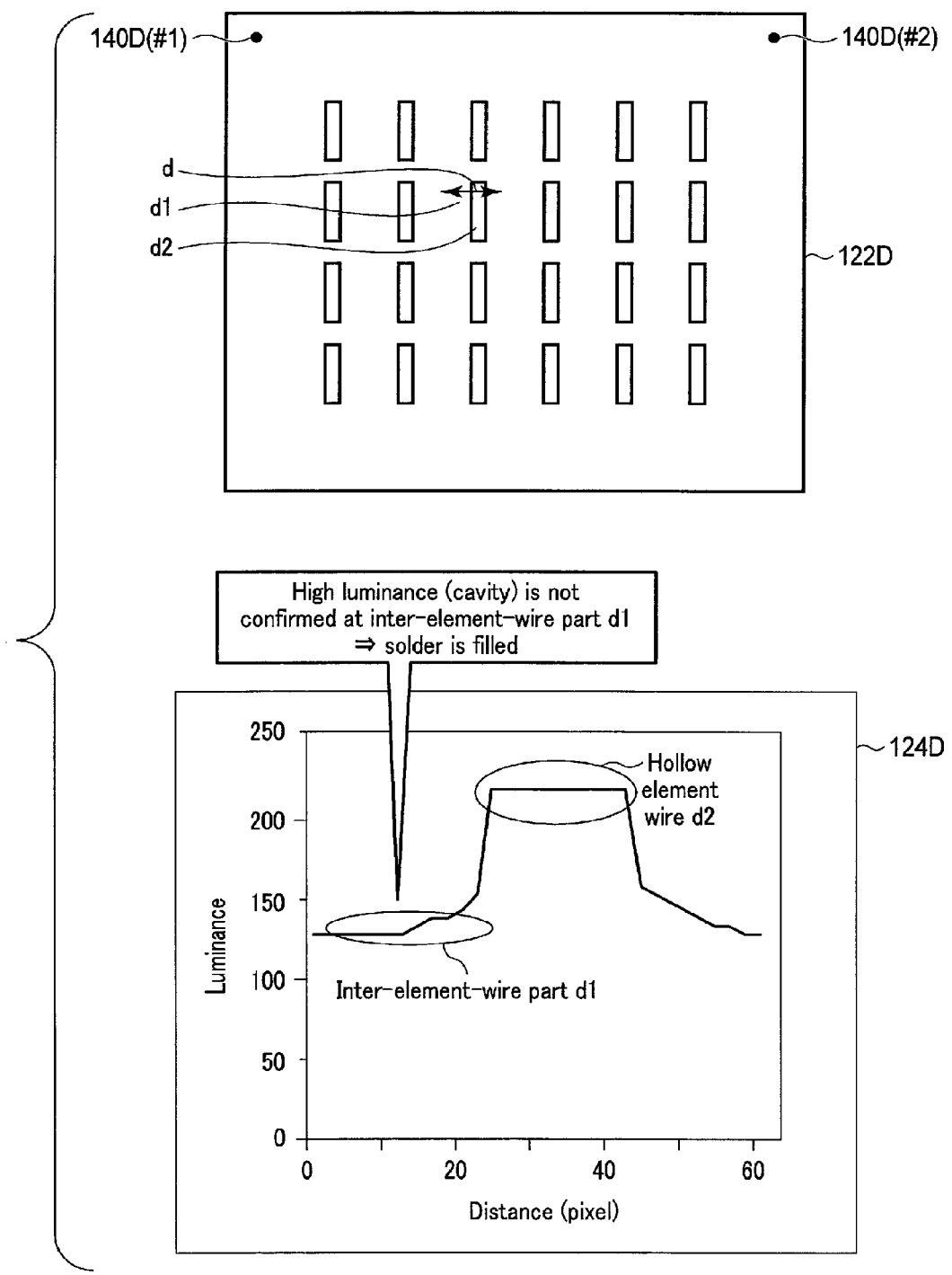
F I G. 4D

| Partial specimen | Thickness of partial specimen (mm) | Luminance value | Braze bonding length (mm) | Determination reference |
|---|---|---|---|---|
| A | f1 | g1 | h1 | |
| B | f2 | g2 | h2 | |
| C | f3 | g3 | h3 | |
| D | f4 | g4 | h4 | |
| | | Total | H | >I |

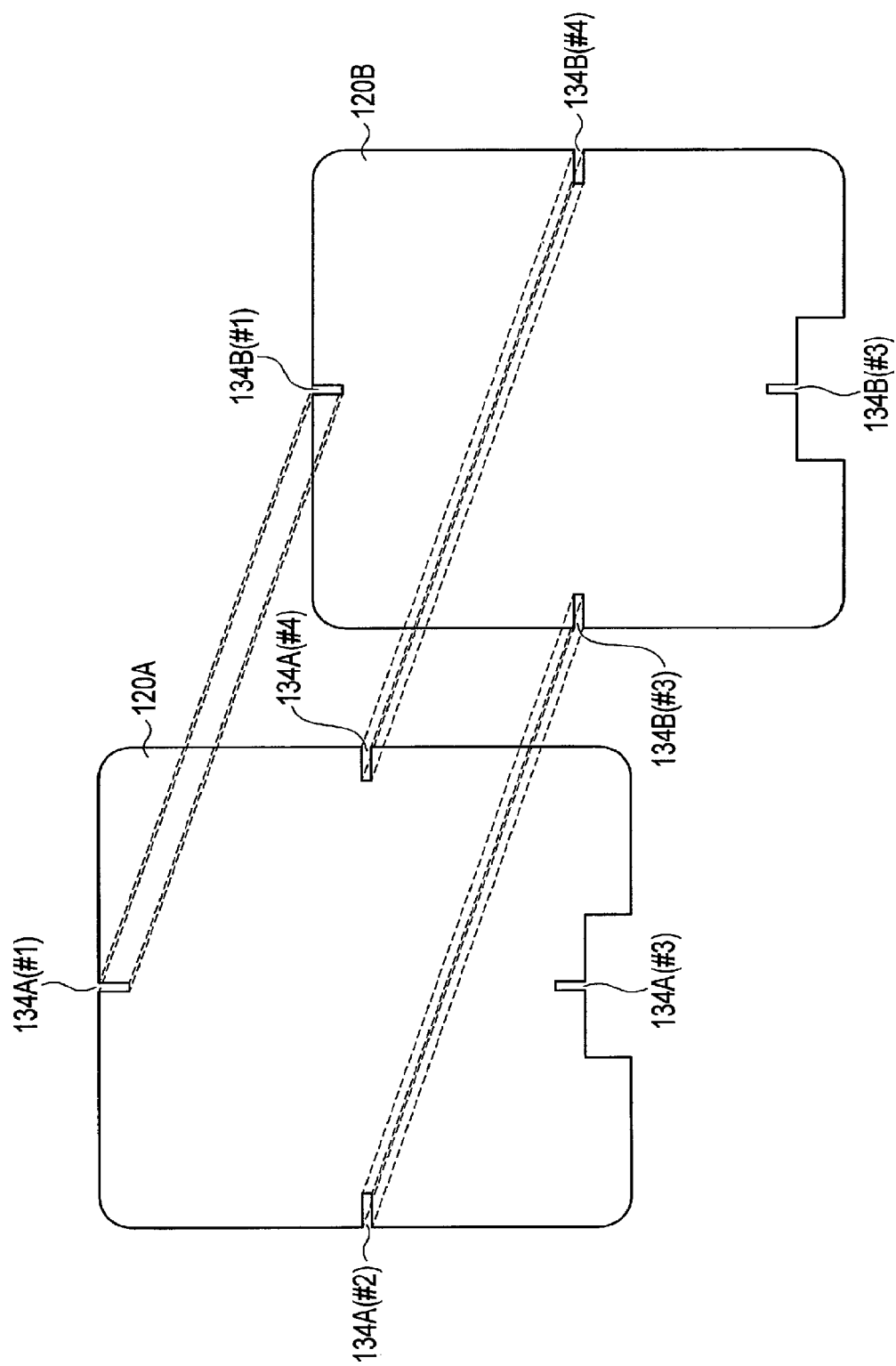
F I G. 13

APPARATUS AND METHOD FOR QUANTITATIVE EVALUATION OF BRAZE BONDING LENGTH WITH USE OF RADIATION

CROSS-REFERENCE TO RELATED APPLICATIONS

This application is based upon and claims the benefit of priority from Japanese Patent Application No. 2015-047639, filed Mar. 10, 2015, the entire contents of which are incorporated herein by reference.

FIELD

Embodiments described herein relate to an apparatus and method for quantitative evaluation of a braze bonding length with use of radiation.

BACKGROUND

Braze bonding is widely used for bonding of copper parts. There is a case in which many parts are braze-bonded in a batchwise manner. In addition, when water or the like is let to flow in a part, a bonded part will have a seal function. When many parts are bonded in a batchwise manner with sealing properties, it is important to confirm the state of braze bonding, and it is necessary to recognize a braze bonding length (so-called seal length).

Conventionally, in an inspection of a braze-bonded part, the braze-bonded part is cut, and the presence/absence determination of a defect by visual observation (cross-sectional observation) with use of a microscope or the like, the defect detection by an ultrasonic flaw detection method, or the presence/absence determination of a defect by visual determination of a radiography image, is performed.

However, when only such conventional defect presence/absence determination is performed, the following problems will arise.

Here, a water-cooling coil of an electrical rotating machine is taken as an example, wherein many hollow copper wires and solid wires are braze-bonded together to a copper-made water chamber part. In the braze bonding, in order to infiltrate molten solder by utilizing a capillary phenomenon of the molten solder, a narrow gap of 0.05 mm to 0.25 mm is usually adopted as the gap between copper wires. A defect of braze bonding (for instance, a part where solder failed to infiltrate, a bubble occurring in solder, a shrinkage cavity, or a crack of solder), which occurs in such a narrow gap, will necessarily become smaller than the narrow gap, and it is not possible to quantitatively evaluate the braze bonding length by visual observation or the like.

There are various modes in shape of defects occurring due to braze bonding. In order to secure a seal length, it is necessary to quantitatively evaluate, regardless of the shape of a defect, the bonding length of solder which fills the narrow gap at the braze-bonded part.

However, in the conventional defect presence/absence determination, although qualitative determination, such as determination as to whether there is a defect in a braze-bonded part, can be performed, quantitative determination as to how long braze bonding is made is not performed.

This being the case, in order to evaluate a seal function by braze bonding, there is a demand for an apparatus and method for performing not only qualitative evaluation, such as simply confirming a braze bonding state, but also quantitative determination of a braze bonding length (so-called seal length).

BRIEF DESCRIPTION OF THE DRAWINGS

FIG. 3 is a conceptual view illustrating an example of a partial specimen fixing unit which is applied to the braze bonding length quantitative evaluation apparatus of the first embodiment;

FIG. 4A is a view illustrating an example of an image (upper part) captured by photographing a partial specimen A, and an example of a one-dimensional luminance (gray levels 0 to 255) distribution (lower part) along a line a;

FIG. 4B is a view illustrating an example of an image (upper part) captured by photographing a partial specimen B, and an example of a one-dimensional luminance (gray levels 0 to 255) distribution (lower part) along a line b;

FIG. 4D is a view illustrating an example of an image (upper part) captured by photographing the partial specimen D, and an example of a one-dimensional luminance (gray levels 0 to 255) distribution (lower part) along a line d;

FIG. 13 is a conceptual view for describing an example of alignment with use of slits.

DETAILED DESCRIPTION

In general, according to one embodiment, a braze bonding length quantitative evaluation apparatus is provided. This apparatus is an apparatus which quantitatively evaluates a braze bonding length of a specimen by using radiation, and includes a radiation emission unit, a light generator, an imaging unit, and a calculator.

The radiation emission unit is configured to emit radiation in a braze bonding length direction to each of a plurality of partial specimens which are obtained by cutting the specimen in a plane perpendicular to the braze bonding length direction.

The light generator is configured to generate light of an amount corresponding to an intensity of transmissive radiation which is part of the radiation emitted by the radiation emission unit, the part of the radiation having passed through each of the partial specimens.

The imaging unit is configured to photograph the light generated by the light generator in accordance with the intensity of the transmissive radiation.

The calculator is configured to calculate a braze bonding length of each of the partial specimens, from a light amount recognized from a photographed result obtained by the imaging unit with respect to each of the partial specimens, based on a pre-acquired correlation between a braze bonding length and a light amount, and to calculate the braze bonding length of the specimen by totaling the calculated braze bonding lengths of the respective partial specimens.

Various embodiments will be described hereinafter with reference to the accompanying drawings.

First Embodiment

Figure 1:
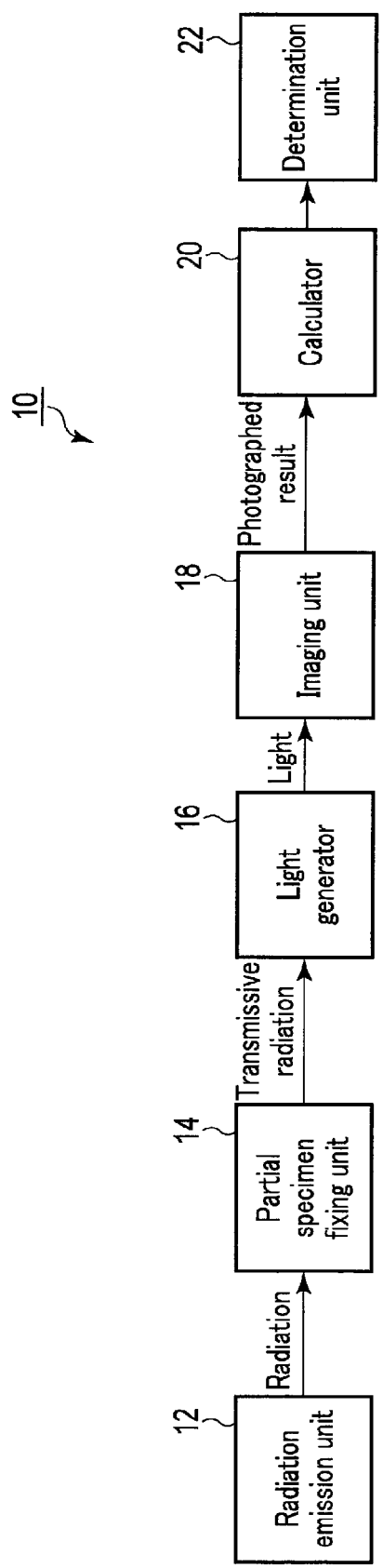
FIG. 1 is a conceptual view illustrating a configuration example of a braze bonding length quantitative evaluation apparatus to which a braze bonding length quantitative evaluation method of a first embodiment is applied.

FIG. 1 is a conceptual view illustrating a configuration example of a braze bonding length quantitative evaluation apparatus 10 to which a braze bonding length quantitative evaluation method of a first embodiment is applied.

Specifically, the braze bonding length quantitative evaluation apparatus 10 of the first embodiment is an apparatus which quantitatively evaluates the braze bonding length of a specimen by using radiation. The braze bonding length quantitative evaluation apparatus 10 includes a radiation emission unit 12, a partial specimen fixing unit 14, a light generator 16, an imaging unit 18, a calculator 20, and a determination unit 22.

Figure 2:
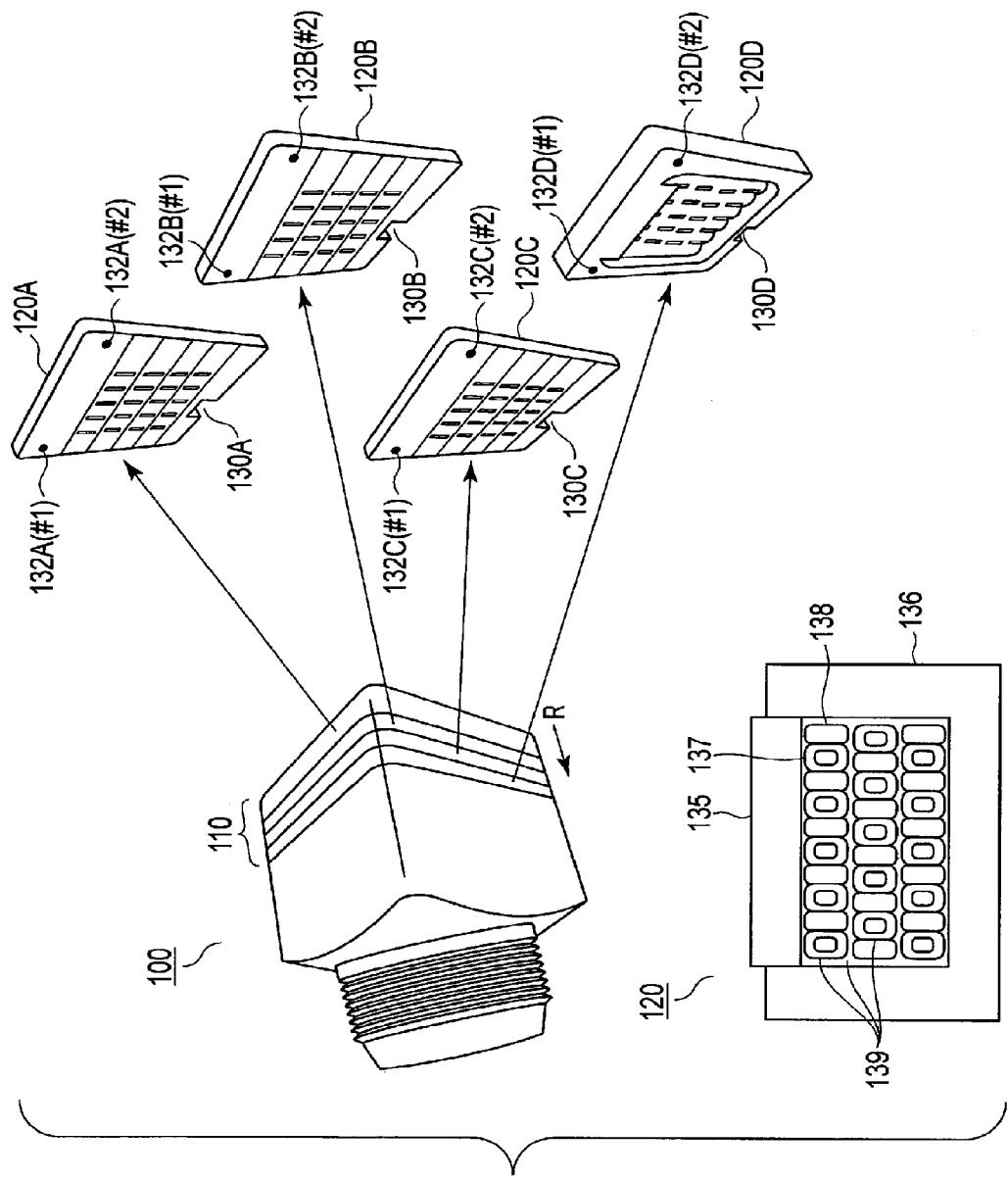
FIG. 2 is a conceptual view illustrating an example of a specimen and partial specimens which are provided to the braze bonding length quantitative evaluation apparatus of the first embodiment.

The radiation emission unit 12, as illustrated in FIG. 2, emits radiation in a braze bonding length direction R to each of a plurality of partial specimens 120A to 120D which are formed by cutting a specimen 110 in a slice shape in a plane perpendicular to the braze bonding length direction R. As the radiation, X rays are preferable, but the radiation is not limited to X rays, and other suitable radiation, such as gamma rays, may be used in accordance with the material, etc. of the specimen 110.

The specimen 110 is a part of a mockup 100 of an actual device, the mockup 100 being braze-bonded under the same conditions as the actual device. Specifically, in the braze bonding length quantitative evaluation apparatus 10 of this embodiment, the braze bonding length is quantitatively evaluated based on transmission characteristics of radiation. For this reason, radiation needs to be emitted onto each of the partial specimens 120A to 120D into which the specimen 110 was cut in slice shapes, and the embodiment cannot directly be applied to the actual device. Thus, to begin with, the mockup 100, which is identical to the actual device, is fabricated, and braze bonding is performed on this mockup 100 under the same conditions as the actual device. Thereafter, of the mockup 100, a part of the specimen 110 is cut in slice shapes, as illustrated in FIG. 2, thereby obtaining the partial specimens 120A to 120D, and radiation is emitted on each of the partial specimens 120A to 120D. The thickness of each partial specimen 120, which is obtained by the cutting, is determined such that, for example, 90% or more of the radiation, which is emitted by the radiation emission unit 12, may not be absorbed by each partial specimen 120. The reason for this is that if 90% or more of the radiation, which is emitted by the radiation emission unit 12, is absorbed by each partial specimen 120, braze bonding length quantitative evaluation, to which a luminance gradation (to be described later) is applied, may become impossible.

Accordingly, the example illustrated in FIG. 2 is merely an example in which four partial specimens 120A to 120D were obtained as a result of the slicing of the specimen 110 with such a length that, for example, 90% or more of the radiation, which is emitted by the radiation emission unit 12, may not be absorbed by each partial specimen 120.

In the meantime, FIG. 2 shows an example of the application of the present embodiment, and illustrates a water-cooling coil of an electrical rotating machine, wherein many hollow copper wires 137 and solid copper wires 138 are braze-bonded together to a copper-made water chamber part. Evaluation target locations in this example are braze-bonded parts 139 illustrated in FIG. 2 (lower part), which are gaps between a clip cover 135, a clip 136, hollow copper wires 137 and solid copper wires 138.

As illustrated in FIG. 3, the partial specimen fixing unit 14 is a part for fixing the partial specimen, 120A to 120D, to which radiation is emitted by the radiation emission unit 12. The specimen 110 is provided with a notch 130 in advance, so that radiation can be emitted under the same conditions, no matter which of the partial specimen 120A to 120D is the partial specimen 120 to which the radiation is emitted. Thereby, when the partial specimens 120A to 120D are cut out of the specimen 110, the respective partial specimens 120A to 120D are provided with notches 130A to 130D at the same corresponding part, as illustrated in FIG. 2.

A projection portion 15A, which corresponds to the notch 130, is provided on the partial specimen fixing unit 14. When the partial specimen 120 is fixed to the partial specimen fixing unit 14, the fixing is performed by fitting the projection portion 15A in the notch 130 and holding the partial specimen 120 by a pair of holders 15B from the front and rear sides. Thereby, radiation is emitted on the respective partial specimens 120A to 120D under the same positional condition. Although FIG. 3 illustrates only the holder 15B which holds the front side of the partial specimen 120, there is also a holder 15B which holds the rear side of the partial specimen 120.

The light generator 16 generates light of an amount corresponding to the intensity of transmissive radiation. The transmissive radiation is that part of the radiation emitted by the radiation emission unit 12, which has passed through the partial specimen 120 (one of partial specimens 120A to 120D) fixed on the partial specimen fixing unit 14.

The imaging unit 18 photographs the light generated by the light generator 16.

For example, when an X-ray generator is used as the radiation emission unit 12, the light generator 16 should preferably be an X-ray color scintillator. In this case, the X-ray color scintillator generates visible light of an amount proportional to the intensity of the transmissive X rays which have passed through the partial specimen 120 (any one of partial specimens 120A to 120D). The X rays, which are emitted from the X-ray generator to the partial specimen 120, attenuate in accordance with the length of a material, which constitutes the partial specimen 120, and an X-ray absorption coefficient in this material. Accordingly, the amount of visible light, which is generated by the X-ray color scintillator, will have a two-dimensional distribution corresponding to the thickness of solder distributed on a two-dimensional plane of the partial specimen 120 (i.e. the length in the braze bonding length direction R). Hence, an image captured by the imaging unit 18 will have a two-dimensional luminance distribution in which luminance differs in accordance with the thickness of solder distributed on the two-dimensional plane.

For example, at a location where the thickness of solder is small, since the absorption of X-rays is small, display is effected at a higher luminance than a location where the thickness of solder is large and a location of a solid bonded material. FIG. 4A to FIG. 4D are conceptual views illustrating examples of this.

Figure 4A:
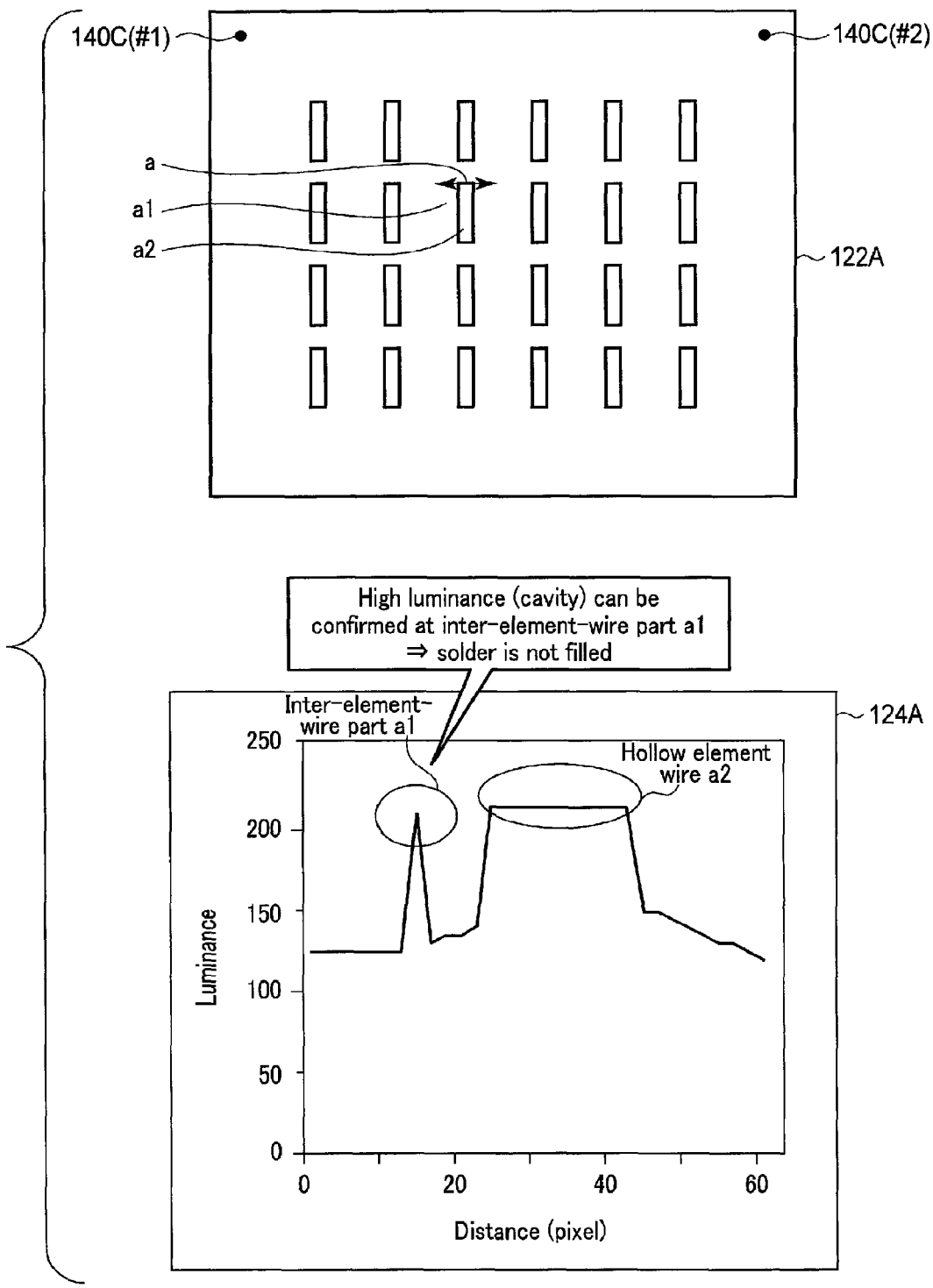

FIG. 4A illustrates an image 122A (upper part) captured by photographing the partial specimen 120A, and a one-dimensional luminance (gray levels 0 to 255) distribution 124A (lower part) along a line a. From the lower part of FIG. 4A, it is confirmed that a high-luminance spike appears at an inter-element-wire part a1. Based on this spike, it is estimated that solder is not filled in the inter-element-wire part a1, and there is a cavity in the inter-element-wire part a1. In the meantime, since no solder is filled in a hollow element wire a2 from the beginning, a high luminance is similarly indicated.

FIG. 4B illustrates an image 122B (upper part) captured by photographing the partial specimen 120B, and a one-dimensional luminance (gray levels 0 to 255) distribution 124B (lower part) along a line b. From the lower part of FIG. 4B, a high-luminance spike is not confirmed at an inter-element-wire part b1. It is thus estimated that solder is filled in the inter-element-wire part b1. In the meantime, since no solder is filled in a hollow element wire b2, a high luminance is similarly indicated.

Figure 4C:
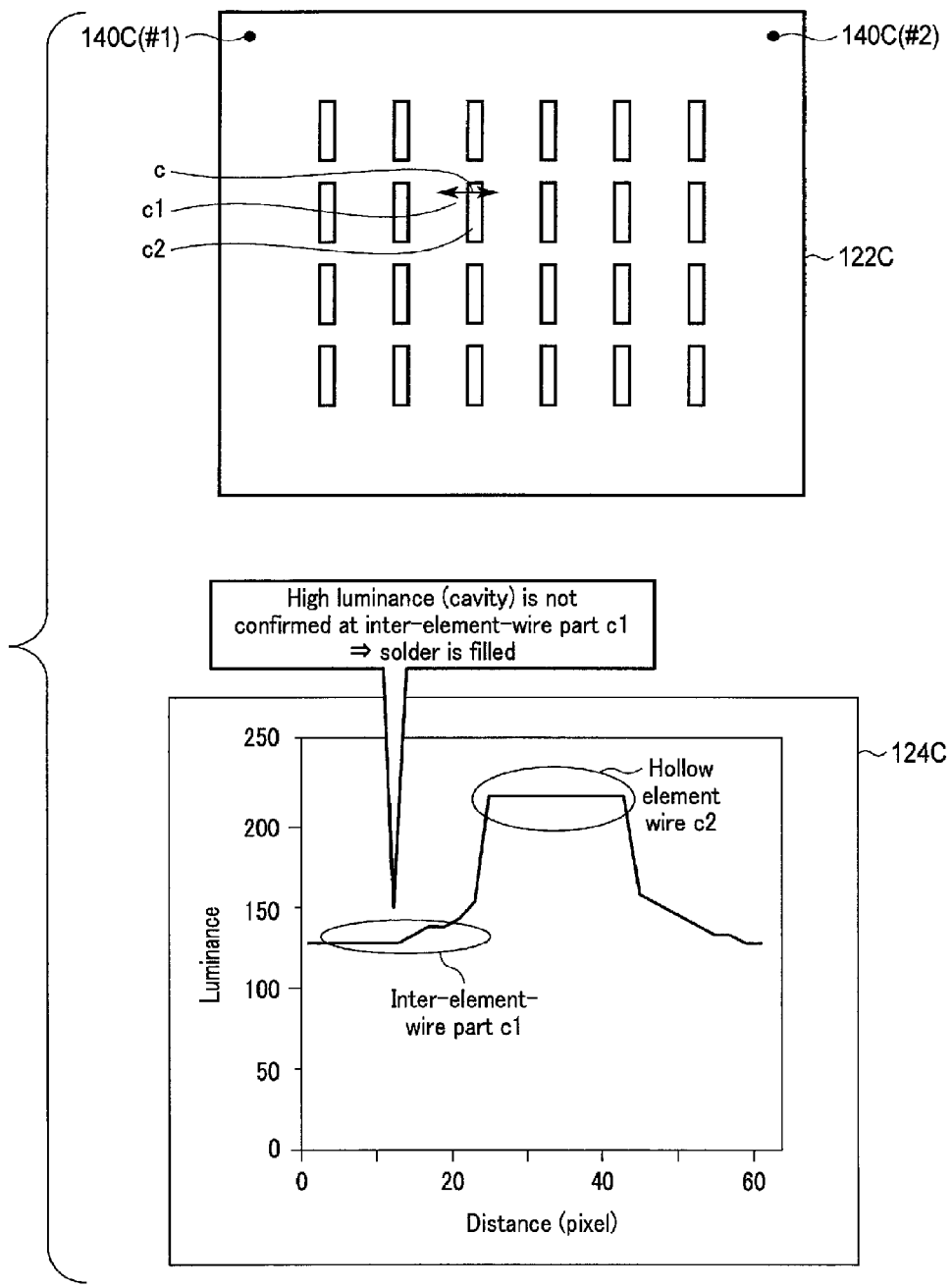
FIG. 4C is a view illustrating an example of an image (upper part) captured by photographing a partial specimen C, and an example of a one-dimensional luminance (gray levels 0 to 255) distribution (lower part) along a line c.

FIG. 4C illustrates an image 122C (upper part) captured by photographing the partial specimen 120C, and a one-dimensional luminance (gray levels 0 to 255) distribution 124C (lower part) along a line c. From the lower part of FIG. 4C, a high-luminance spike is not confirmed at an inter-element-wire part c1. It is thus estimated that solder is filled in the inter-element-wire part c1. In the meantime, since no solder is filled in a hollow element wire c2, a high luminance is similarly indicated.

FIG. 4D illustrates an image 122D (upper part) captured by photographing the partial specimen 120D, and a one-dimensional luminance (gray levels 0 to 255) distribution 124D (lower part) along a line d. From the lower part of FIG. 4D, a high-luminance spike is not confirmed at an inter-element-wire part d1. It is thus estimated that solder is filled in the inter-element-wire part d1. Incidentally, since no solder is filled in a hollow element wire d2, a high luminance is similarly indicated.

In the meantime, the luminance distributions 124A to 124D of the respective partial specimens 120A to 120D, as illustrated in the lower parts of FIG. 4A to FIG. 4D, are obtained under the same conditions. Specifically, when an X-ray generator is used as the radiation emission unit 12, the luminance distributions 124A to 124D are obtained under all identical conditions including the tube voltage and tube current of the X-ray generator, the X-ray irradiation condition such as the quantity of radiation, the fixation position of the partial specimen 120 on the partial specimen fixing unit 14, and the imaging condition such as the magnification of a camera used as the imaging unit 18.

From the luminance distributions 124A to 124D as illustrated in the lower parts of FIG. 4A to FIG. 4D, it becomes possible to recognize not only the distribution of solder on the two-dimensional plane, but also the magnitude of thickness of the solder. With reference to these luminance distributions 124A to 124D, the calculator 20 executes a process to be described below, based on the correlation between the braze bonding length and the luminance (light amount), thereby recognizing the thickness of solder at respective positions (pixels) on the two-dimensional plane of each of the partial specimens 120A to 120D.

To begin with, the correlation between the braze bonding length and the luminance (light amount) is described. The calculator 20 includes a polynomial expression that is a relational expression representing this correlation. This relational expression is obtained in advance in a manner as described below, by using a reference specimen 30 an example of which is illustrated, for example, in FIG. 5A. In addition, FIG. 5B is a front view in a case where FIG. 5A is viewed in the direction of an arrow in FIG. 5A.

The reference specimen 30 is formed of the same material as the solder material at the bonded parts of the specimen 110, or a material having an equal X-ray absorption coefficient (for example, when X rays are used as radiation).

Figure 5A:
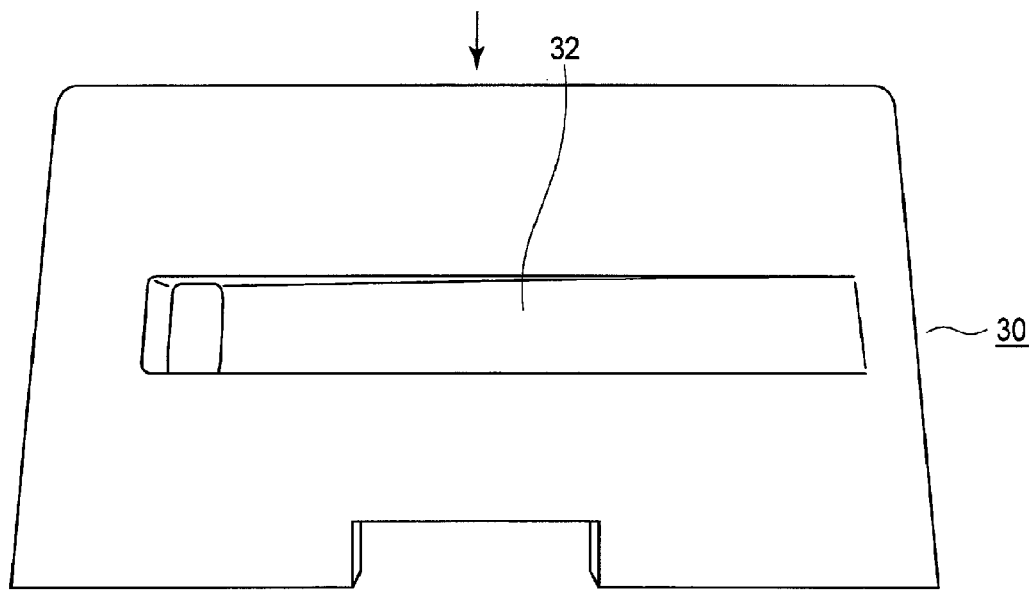
FIG. 5A is a top view illustrating an example of a reference specimen.
Figure 5B:
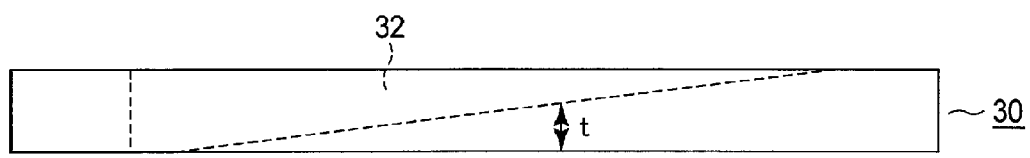
FIG. 5B is a front view illustrating the reference specimen of FIG. 5A, as viewed in the direction of an arrow.

In addition, as illustrated in FIG. 5A and FIG. 5B, the reference specimen 30 is configured such that a thickness t (corresponding to a braze bonding length) varies continuously at a taper portion 32.

As regards the reference specimen 30, the thickness t at an arbitrary part of the taper portion 32 is known in advance.

This reference specimen 30 is fixed to the partial specimen fixing unit 14, and a luminance distribution is obtained under all identical conditions including the X-ray irradiation condition, the fixation position on the partial specimen fixing unit 14, and the imaging condition such as the magnification of a camera used as the imaging unit 18.

Based on the obtained result, luminances corresponding to various braze bonding lengths can be obtained. Thus, a relational expression, which represents the correlation between the braze bonding length and the luminance (light amount), is obtained.

Figure 6A:
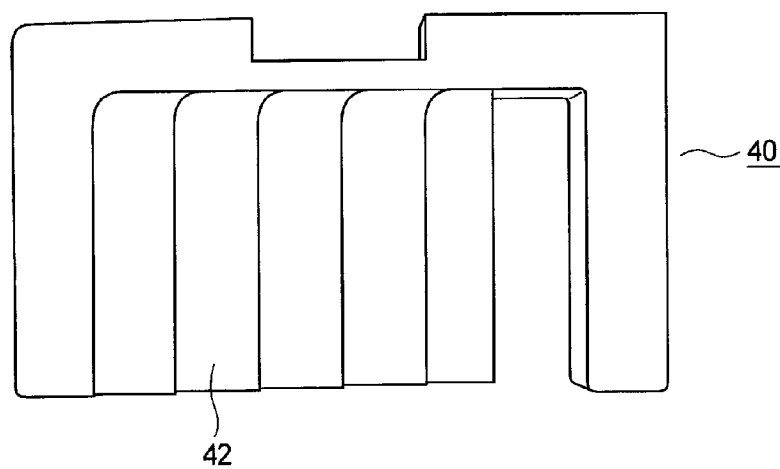
FIG. 6A is a top view illustrating another example of the reference specimen.
Figure 6B:
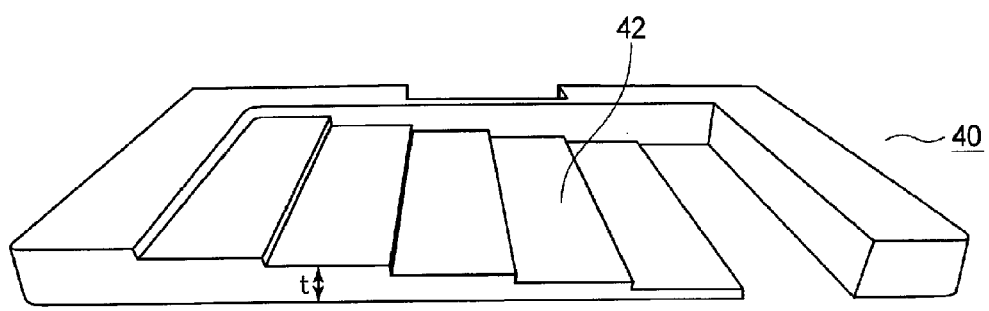
FIG. 6B is a perspective view of the reference specimen of FIG. 6A.

The structure of the reference specimen is not limited to the structure shown in FIG. 5A and FIG. 5B. A modification of the reference specimen is described with reference to FIG. 6A and FIG. 6B. A reference specimen 40 illustrated in FIG. 6A and FIG. 6B includes, in place of the taper portion 32, a stepped portion 42 having a thickness t (corresponding to a braze bonding length) which varies stepwise. As regards the reference specimen 40, too, the thickness t at an arbitrary part of the stepped portion 42 is known in advance.

From a luminance distribution obtained with respect to the reference specimen 40, luminance values corresponding to a plurality of braze bonding lengths (seven points in the example shown in FIG. 6A and FIG. 6B) can also be obtained, although the braze bonding length varies discontinuously. Thus, a relational expression, which represents the correlation between the braze bonding length and the luminance (light amount), is similarly obtained.

The following equation is a polynomial expression showing an example of the relational expression representing the correlation between a braze bonding length f(x) and a luminance (light amount) x.

$$f(x)=ax^m+bx^{m-1}+cx^{m-2}+dx^{m-3}+ex^{m-4}+fx^{m-5}+\ldots+nx+A \quad \text{(equation 1)}$$

Using this polynomial expression, the calculator 20 calculates, from the luminance distributions of the partial specimens 120A to 120D, the thicknesses of braze bonding at respective pixels on the two-dimensional plane of each of the partial specimens 120A to 120D. In the meantime, for the purpose of simple description, the luminance distributions 124A to 214D illustrated in the lower parts of FIG. 4A to FIG. 4D are only examples of one-dimensional luminance distributions. However, the imaging unit 18 has luminance values at respective pixels on the two-dimensional planes of the partial specimens 120A to 120D.

In addition, the calculator 20 totals, with respect to each identical pixel, the calculated braze bonding thicknesses at the respective pixels on the two-dimensional planes of the partial specimens 120A to 120D. Thereby, the calculator 20 calculates the braze bonding length in the braze bonding length direction R at each pixel on the two-dimensional plane of the entirety of the specimen 110.

In the meantime, in order to prevent misalignment of pixels at the time of totaling, the respective partial specimens 120A to 120D may, as illustrated in FIG. 2, be provided with pinholes 132(#1) and 132(#2) for alignment.

By providing the pinholes 132 (#1) and 132 (#2), spots 140(#1) and 140(#2) corresponding to the pinholes 132 (#1) and 132 (#2) appear on the image, as illustrated in FIG. 4A to FIG. 4D. Since the pinhole 132 (#1), 132 (#2) is a cavity, no brazing is made in the pinhole 132 (#1), 132 (#2), and, moreover, since the pinhole 132 (#1), 132 (#2) has a luminance value that is conspicuously different from the luminance of the vicinity thereof, the discrimination of the corresponding pixel is easy.

Figure 12:
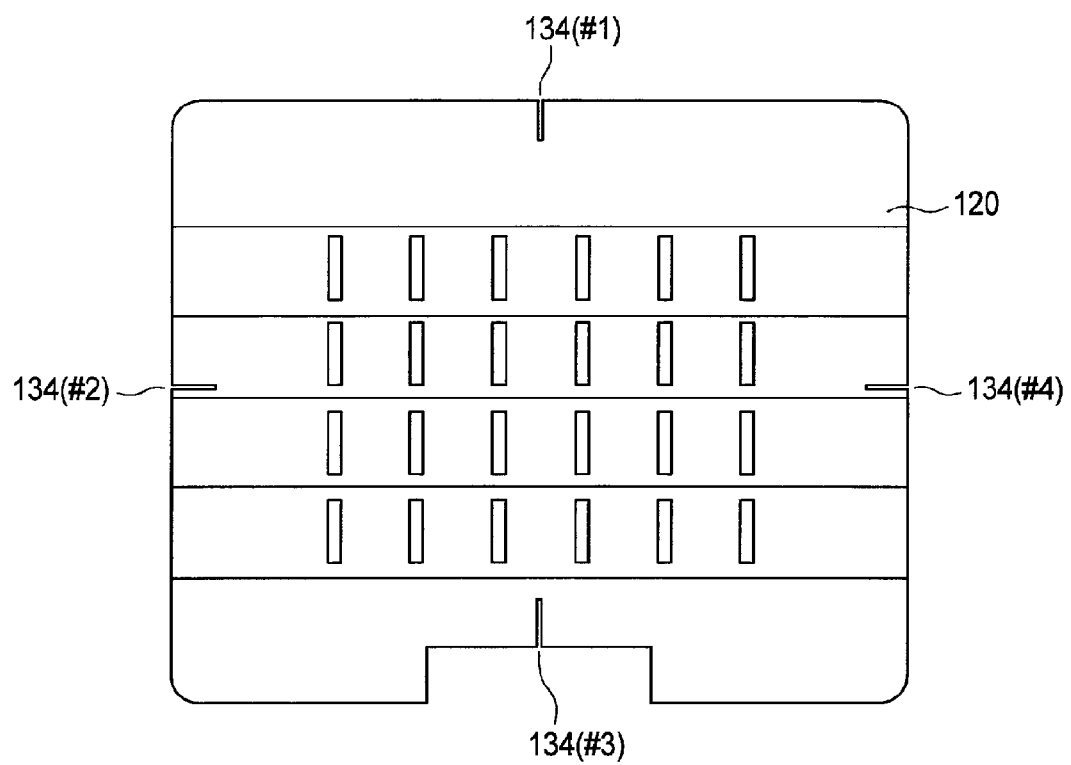
FIG. 12 is a conceptual view illustrating an example of a partial specimen in which slits, in place of pinholes, are provided.

In the meantime, as illustrated in FIG. 12, slits 134 (#1~#4) may be provided instead of the pinholes 132. Even when the slits 134(#1~#4) are provided, the slits 134(#1~#4) can be used for alignment, as illustrated in FIG. 13.

Hence, at the time of the totaling, the totaling is performed while making coincident the pixels corresponding to the pinholes 132(#1) and 132(#2), with respect to the pixels on the two-dimensional planes of the respective partial specimens 120A to 120D. Thereby, the braze bonding thicknesses in the two-dimensional planes of the respective partial specimens 120A to 120D can exactly be totaled with respect to each identical pixel.

Figures 7, 8A:
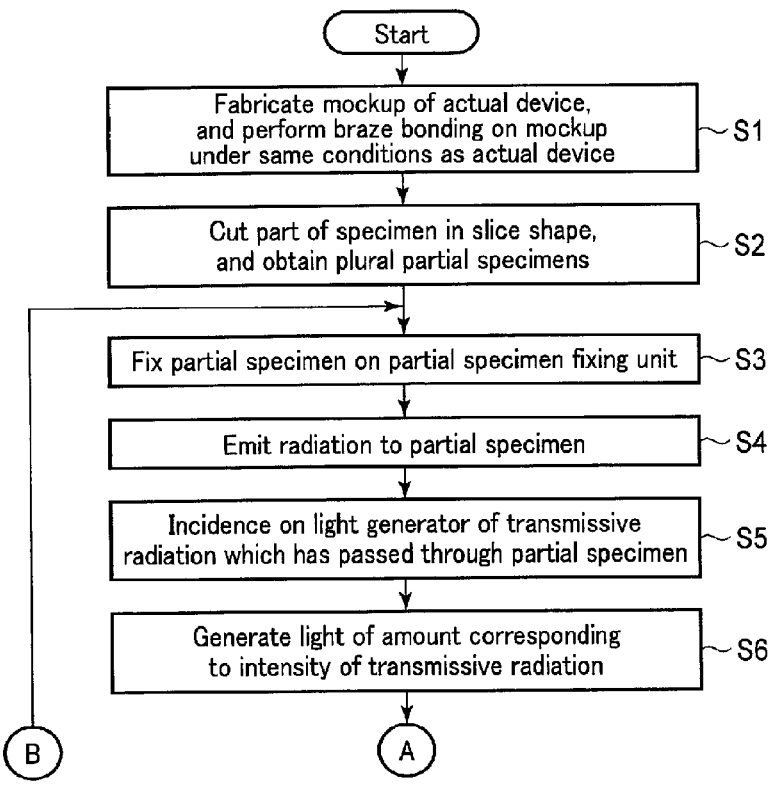
FIG. 7 is a view illustrating an example of results on the braze bonding lengths at certain pixels of a specimen including four partial specimens.
FIG. 8A is a flowchart (first half) illustrating an operation example of the braze bonding length quantitative evaluation apparatus of the first embodiment.

FIG. 7 is a view illustrating an example of results on the braze bonding lengths at certain pixels of the specimen 120, which were calculated by the calculator 20.

The four partial specimens 120A to 120D as shown in FIG. 2 are employed as partial specimens e, and with respect to each of the four partial specimens 120A to 120D, a partial specimen thickness f, a luminance value g, and a braze bonding length (thickness) h are shown. For example, in the case of the partial specimen 120A, it is indicated that the thickness is f1 (mm), the luminance value is g1, and the braze bonding length, which was calculated from this luminance value, is h1 (mm). If the braze bonding length h1 (mm) of this partial specimen 120A is added to all the braze bonding lengths h2, h3 and h4 (mm) of the other partial specimens 120B to 120D, H (mm) is obtained as the total braze bonding length.

For example, it is assumed that, in a certain actual device, the braze bonding length of a part corresponding to the specimen 120 needs to exceed I (mm). If the braze bonding length H (mm) of the specimen 120 exceeds the bonding length reference value I (mm), the determination unit 22 determines that, in the actual device, too, the braze bonding length h of the part corresponding to the specimen 120 satisfies a determination reference i.

Figure 8B:
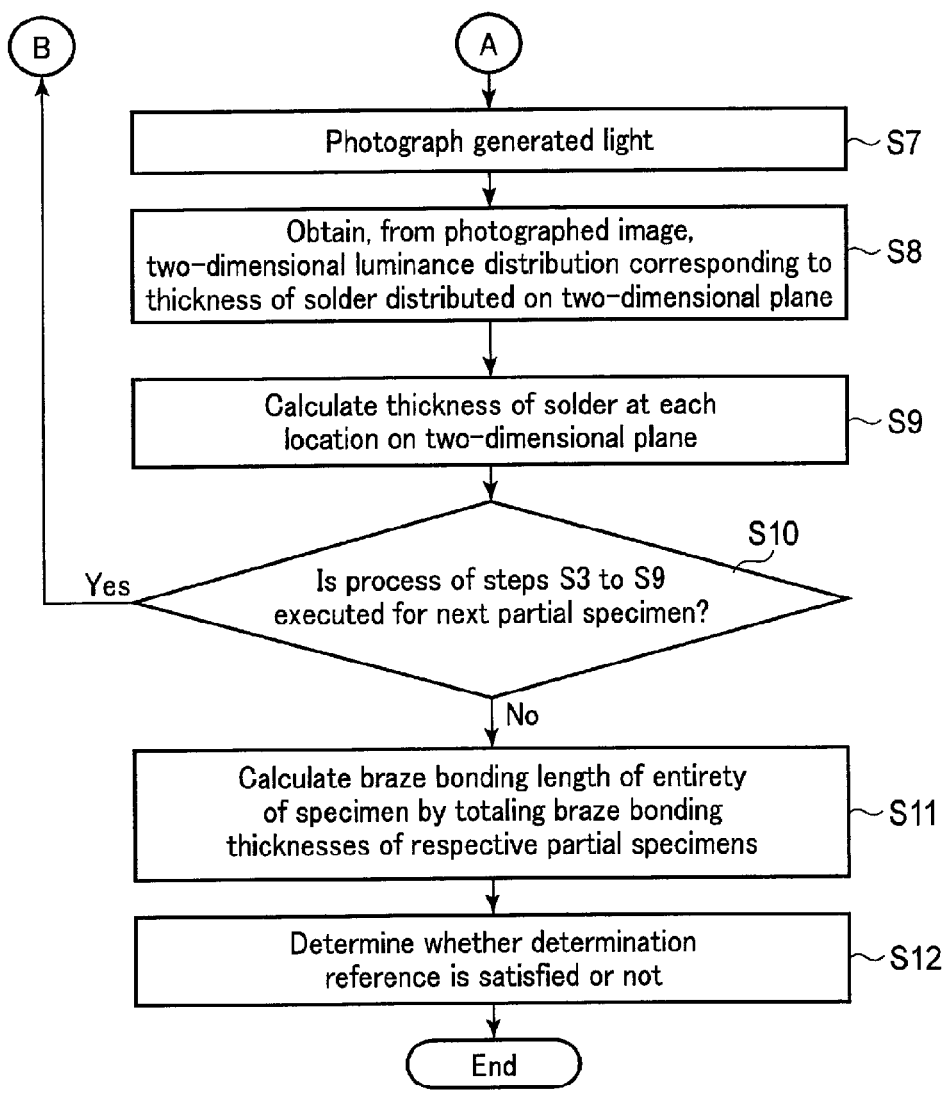
FIG. 8B is a flowchart (second half) illustrating the operation example of the braze bonding length quantitative evaluation apparatus of the first embodiment.

Next, referring to flowcharts of FIG. 8A and FIG. 8B, a description is given of the operation of the braze bonding length quantitative evaluation apparatus 10 to which the braze bonding length quantitative evaluation method of the embodiment with the above-described structure is applied.

Specifically, in order to perform braze bonding length quantitative evaluation by using the braze bonding length quantitative evaluation apparatus 10, a mockup 100 of the actual device, which includes a part of an evaluation target, is first fabricated, and braze bonding is performed on this mockup 100 under the same conditions as the actual device (S1).

Next, the part of the specimen 110 of the mockup 100 is cut into slices, as illustrated in FIG. 2, and a plurality of partial specimens 120A to 120D are obtained (S2). In the meantime, the thickness of each partial specimen 120, which is obtained by the cutting, is determined such that, for example, 90% or more of the radiation, which is emitted by the radiation emission unit 12, may not be absorbed by each partial specimen 120, thereby to enable braze bonding length quantitative evaluation to which a luminance gradation (to be described later) is applied. In the description below, as illustrated in FIG. 2, a description is given of the example in which four partial specimens 120A to 120D were obtained as a result of the slicing of the specimen 110.

Radiation is emitted by the radiation emission unit 12 to each of the four partial specimens 120A to 120D which were obtained by the slicing. By transmissive radiation of the emitted radiation, light is generated by the light generator 16, and the light is photographed by the imaging unit 18. Based on the photographed result, the calculator 20 calculates the braze bonding length.

In the description below, a description is given on the assumption that the series of processes are executed in the order of the partial specimen 120A→120B→120C→120D. However, for example, the series of processes may be executed in any order, such as 120D→120C→120B→120A, or 120A→120C→120D→120B.

To start with, the partial specimen 120A, which is the first partial specimen 120, is fixed on the partial specimen fixing unit 14 (S3). Specifically, the notch 130 of the partial specimen 120A is engaged with the projection portion 15A, and the front and rear sides of the partial specimen 120 are fixed by the paired holders 15B.

In addition, radiation is emitted from the radiation emission unit 12 to the fixed partial segment 120A (S4).

Then, transmissive radiation, which has passed through the partial specimen 120A, reaches the light generator 16 (S5).

The light generator 16 generates light of an amount corresponding to the intensity of the transmissive radiation (S6).

The imaging unit 18 photographs the light generated by the light generator 16 (S7).

For example, when an X-ray generator is used as the radiation emission unit 12, an X-ray color scintillator is used as the light generator 16. In this case, the X-ray color scintillator generates visible light of an amount proportional to the intensity of the transmissive X rays which have passed through the partial specimen 120A. The X rays, which are emitted from the X-ray generator to the partial specimen 120, attenuate in accordance with the length of a material, which constitutes the partial specimen 120, and an X-ray absorption coefficient in this material. Accordingly, the amount of visible light, which is generated by the X-ray color scintillator, has a two-dimensional distribution corresponding to the thickness of solder distributed on the two-dimensional plane of the partial specimen 120 (i.e. the length in the braze bonding length direction R).

In this manner, from the image captured by the imaging unit 18, a two-dimensional luminance distribution 124A, for example, as illustrated in the lower part of FIG. 4A, is obtained in accordance with the thickness of solder distributed on the two-dimensional plane (S8).

The calculator 20 calculates, from this luminance distribution 124A, the thickness of solder at respective positions (pixels) on the two-dimensional plane of the partial specimen 120A, based on the correlation between the braze bonding length and the luminance (light amount) as indicated in the above-described equation 1 (S9).

Then, with respect to the next partial specimen, 120B to 120D, the process of steps S3 to S9 is executed, and the thickness of solder at respective positions (pixels) on the two-dimensional plane is calculated (S10: Yes). In the meantime, the process of steps S3 to S9 is executed under the identical conditions with respect to the partial specimens 120A to 120D. For example, when an X-ray generator is used as the radiation emission unit 12, the process of steps S3 to S9 is executed under all identical conditions including the tube voltage and tube current of the X-ray generator, the X-ray irradiation condition such as the quantity of radiation, the fixation position of the partial specimen 120 on the partial specimen fixing unit 14, and the imaging condition such as the magnification of a camera used as the imaging unit 18.

In this manner, if the processes for all partial specimens 120A to 120D are completed (S10: No), the calculator 20 further totals, with respect to each identical pixel, the braze bonding thicknesses at the respective pixels on the two-dimensional planes of the partial specimens 120A to 120D. Thereby, the calculator 20 calculates the braze bonding length in the braze bonding length direction R at each pixel on the two-dimensional plane of the entirety of the specimen 110 (S11).

In the meantime, as described above, the respective partial specimens 120A to 120D are provided with the pinholes 132(#1) and 132(#2) for alignment, as illustrated in FIG. 2, or the slits 134(#1~#4) for alignment, as illustrated in FIG. 12. Thereby, the totaling at the identical pixels of the partial specimens 120A to 120D is executed without misalignment of pixels.

Then, the determination unit 22 determines whether the braze bonding length, which was calculated in step S11, satisfies the determination reference or not (S12).

If the determination unit 22 determines that the braze bonding length satisfies the determination reference, it is estimated that, in the actual device, too, the braze bonding length of the part corresponding to the specimen 120 satisfies the determination reference. If the determination unit 22 determines that the braze bonding length does not satisfy the determination reference, it is estimated that the braze bonding length of the part corresponding to the specimen 120 does not satisfy the determination reference in the actual device, either.

As described above, according to the braze bonding length quantitative evaluation apparatus 10 to which the braze bonding length quantitative evaluation method of the present embodiment is applied, in order to quantitatively evaluate the braze bonding length, it is necessary to cut out the part that is to be evaluated. Thus, this evaluation may not directly be applied to the actual device. However, by using, as the evaluation target, the mockup which is identical to the actual device and to which braze bonding was made under the same conditions as the actual device, it becomes possible to quantitatively evaluate the braze bonding length, which was not possible in the conventional art, although the evaluation is indirectly performed.

Furthermore, the bonding length at an arbitrary location on the two-dimensional plane can also be quantitatively evaluated. Thus, for example, even when very many narrow gaps between conductors and conductor coil clips are braze-bonded, as in the case of a water-cooling coil of an electrical rotating machine, the braze bonding lengths at the respective braze-bonded parts can be recognized at a time, it is possible to contribute to enhancing the reliability of the electrical rotating machine.

Second Embodiment

Since a second embodiment is a modification of the first embodiment, only different points from the first embodiment will be described, and an overlapping description is avoided. In addition, in the description below, the same parts as in the first embodiment are denoted by like reference numerals.

Figure 9:
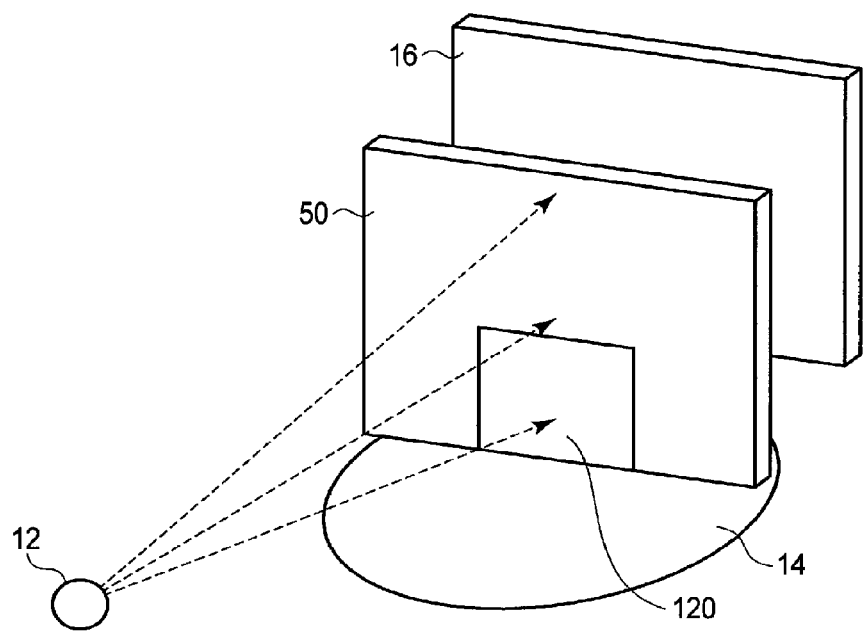
FIG. 9 is a conceptual view for describing an example of a shield plate which is applied to a braze bonding length quantitative evaluation apparatus of a second embodiment.

Specifically, in a braze bonding length quantitative evaluation apparatus to which a braze bonding length quantitative evaluation method of this embodiment is applied, the braze bonding length quantitative evaluation apparatus 10 of the first embodiment is modified such that the surrounding of the partial specimen 120, to which radiation is emitted by the radiation emission unit 12, is covered by a shield plate 50 that absorbs radiation, as illustrated in FIG. 9, so that only transmissive radiation may reach the light generator 16. In FIG. 9, in order to avoid an unnecessary description, the projection portion 15A and holder 15B on the partial specimen fixing unit 14 are omitted.

Figure 10:
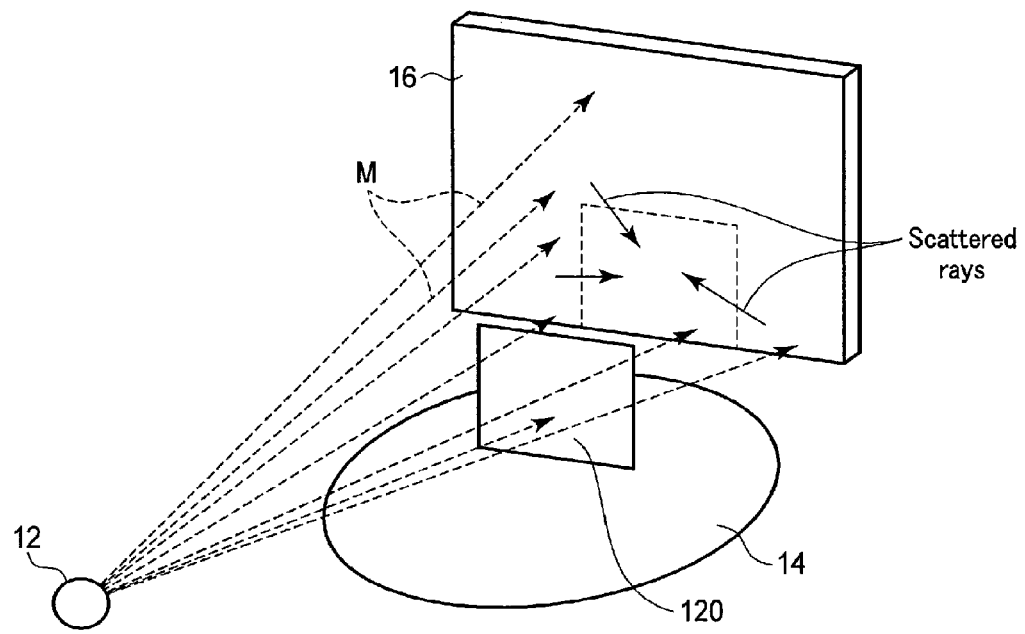
FIG. 10 is a conceptual view for describing a state in which the shield plate is not provided.

FIG. 10 is a view for describing a state in which the shield plate 50 is not used. When radiation is emitted from the radiation emission unit 12 to the partial specimen 120 fixed on the partial specimen fixing unit 14, not only the transmissive radiation, which has passed through the partial specimen 120A, reaches the light generator 16, but also scattered rays due to the radiation, which does not pass through the partial specimen 120A, are incident on the light generator 16, as illustrated in FIG. 10.

The scattered rays, which are incident on the light generator 16 in this manner, are noise which increases a background component of the image of the part of the specimen to be observed, leading to degradation in reliability of the obtained two-dimensional luminance distribution.

However, such noise will not occur by disposing, as illustrated in FIG. 9, the shield plate 50 so that only the transmissive radiation may reach the light generator 16.

According to the braze bonding length quantitative evaluation apparatus to which the braze bonding length quantitative evaluation method of this embodiment is applied, the occurrence of noise can be prevented by applying the above-described shield plate 50.

As a result, the advantageous effects of the first embodiment can be realized while the evaluation precision is further enhanced.

Third Embodiment

Since a third embodiment is a modification of the first or second embodiment, only different points from the first or second embodiment will be described, and an overlapping description is avoided. In addition, in the description below, the same parts as in the first or second embodiment are denoted by like reference numerals.

Specifically, a braze bonding length quantitative evaluation apparatus, to which a braze bonding length quantitative evaluation method of this embodiment is applied, relates to a modification of the imaging unit 18 in the braze bonding length quantitative evaluation apparatus of the first or second embodiment.

In the present embodiment, the imaging unit 18 photographs the light generated by the light generator 16, with respect to each of a plurality of frequency bands. In order to realize this, for example, the imaging unit 18 includes a first camera which is suited to photographing light of a red component, a second camera which is suited to photographing light of a green component, and a third camera which is suited to photographing light of a blue component.

In addition, the calculator 20 calculates the braze bonding length of the specimen 120 by using a photographed result which was captured by any one of these cameras.

An example of determination as to which camera is to be used will be described with reference to FIG. 11A and FIG. 11B.

Figure 11A:
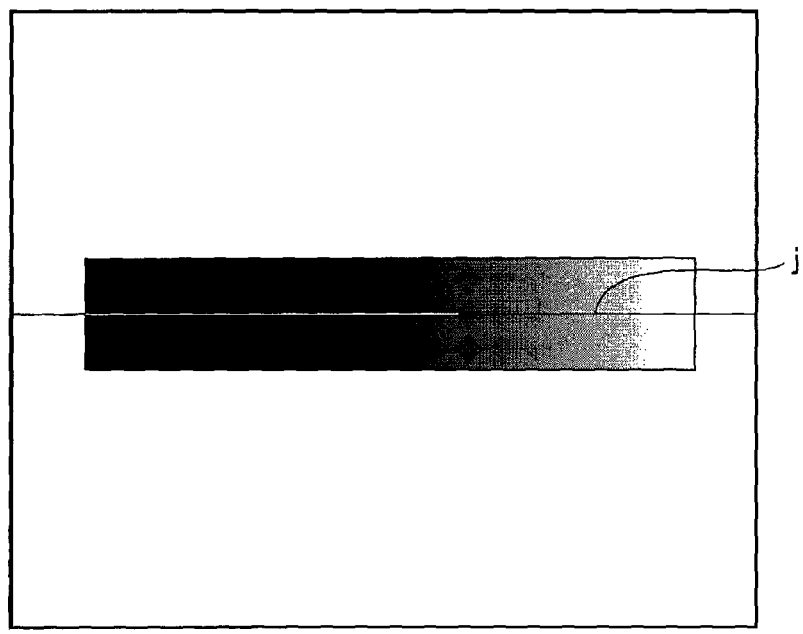
FIG. 11A illustrates an example of an image captured by an imaging unit in the first or second embodiment.

FIG. 11A illustrates an example of an image captured by the imaging unit 18 in the first or second embodiment. FIG. 11B illustrates a luminance (y axis) relative to a position (pixel) (x axis) of an evaluation line j in FIG. 11A. In FIG. 11B, however, the light generated by the light generator 16 is separated into red component light p, green component light q and blue component light r, and the luminance (y axis) relative to the position (x axis) is indicated with respect to each of the component lights.

Figure 11B:
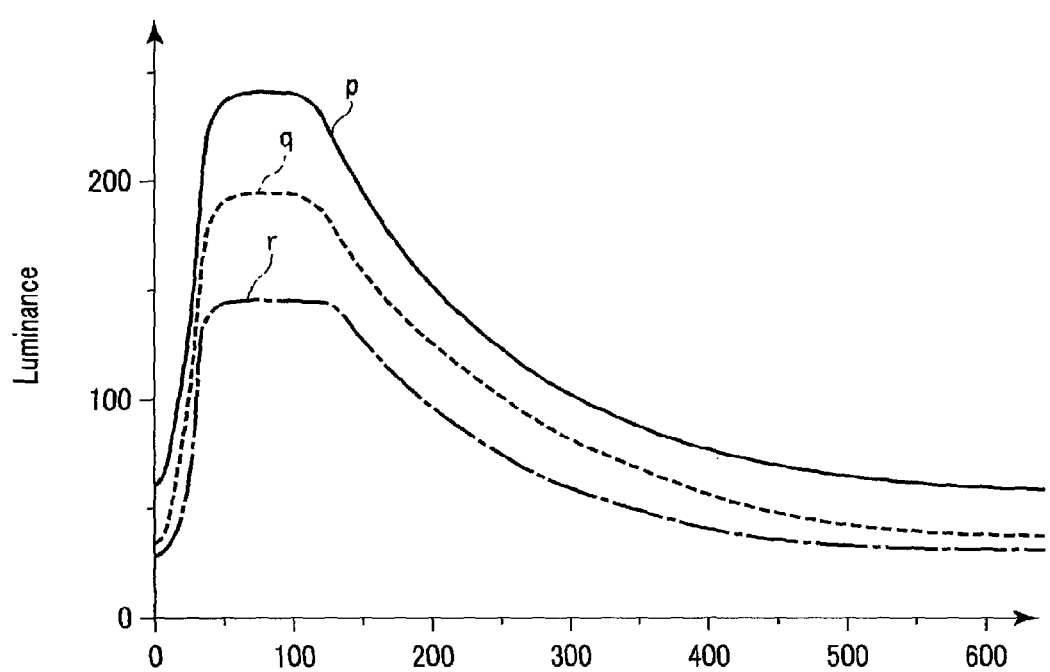
FIG. 11B is an example of a graph illustrating, with respect to three component lights, a luminance (y axis) relative to a position (pixel) (x axis) of an evaluation line j in FIG. 11A.

In FIG. 11B, the read component light p indicates luminance values in a wide range as a whole from a high luminance region to a low luminance region.

On the other hand, since each of the green component light q and blue component light r indicates only low luminance values as a whole, it may be hardly expectable to obtain a high evaluation precision.

Thus, in the case of the characteristic conditions as illustrated in FIG. 11B, it is determined that the evaluation using the red component light p is preferable.

In this manner, in the case of calculating the braze bonding length of the partial specimen 120 by using the photographed result in any one of the plural frequency bands, the calculator 20 needs to have the correlation between the braze bonding length and light amount with respect to each of the frequency bands.

For example, if a description is given by using the example of FIG. 11B, the calculator 20 includes relational expressions representing the correlations between the braze bonding length and light amount, which inherently relate to the red component light p, green component light q and blue component light r, respectively.

This correlation can be obtained by using the reference specimen as described in the first embodiment, and by recognizing the correlation between the thickness of the reference specimen and the luminance with respect to each of the component lights.

In addition, for example, when evaluation is made by using the red component light p as described above, the calculator 20 calculates the braze bonding length from the luminance value of the red component light p, by using the relational expression representing the correlation between the braze bonding length and light amount, which inherently relates to the red component light p.

According to the braze bonding length quantitative evaluation apparatus 10 to which the braze bonding length quantitative evaluation method of the present embodiment is applied, the light generated by the light generator 16 is divided into lights of a plurality of frequency bands, and the braze bonding length can be evaluated by using that one of these lights of plural frequency bands, which is most suitable as evaluation light.

As a result, the advantageous effects of the first or second embodiment can be realized while the evaluation precision is further enhanced.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. An apparatus which quantitatively evaluates a braze bonding length of a specimen by using radiation, comprising:
   a radiation emission unit configured to emit radiation in a braze bonding length direction to each of a plurality of partial specimens which are obtained by cutting the specimen in a plane perpendicular to the braze bonding length direction;
   a light generator configured to generate light of an amount corresponding to an intensity of transmissive radiation which is part of the radiation emitted by the radiation emission unit, the part of the radiation having passed through each of the partial specimens;
   an imaging unit configured to photograph the light generated by the light generator in accordance with the intensity of the transmissive radiation; and
   a calculator configured to calculate a braze bonding length of each of the partial specimens, from a light amount recognized from a photographed result obtained by the imaging unit with respect to each of the partial specimens, based on a correlation between a braze bonding length and a light amount which is pre-acquired, and to calculate the braze bonding length of the specimen by totaling the calculated braze bonding lengths of the respective partial specimens.

2. The apparatus of claim 1, wherein the radiation is X rays.

3. The apparatus of claim 1, wherein the specimen is a part of a mockup of an actual device, and the specimen is braze-bonded under the same condition as the actual device.

4. The apparatus of claim 1, wherein the photographed result by the imaging unit is a two-dimensional image, and each of the partial specimens includes an alignment portion for two-dimensional alignment of each of the partial specimens.

5. The apparatus of claim 1, wherein the correlation is represented by a polynomial expression.

6. The apparatus of claim 1, further comprising a fixing unit configured to fix each of the partial specimens such that the radiation is emitted to each of the partial specimens at an identical position.

7. The apparatus of claim 1, further comprising a shield plate configured to cover a surrounding of the partial specimen to which the radiation is emitted by the radiation emission unit, such that only the transmissive radiation reaches the light generator.

8. The apparatus of claim 1, wherein the imaging unit is configured to photograph the light generated by the light generator, with respect to each of a plurality of frequency bands,
   the correlation is a pre-acquired correlation between the braze bonding length and the light amount with respect to each of the plurality of frequency bands, and
   the calculator is configured to calculate, with respect to a frequency band that is any one of the plurality of frequency bands, the braze bonding length of each of the partial specimens, from a light amount recognized from a photographed result at the frequency band, based on the correlation at the frequency band.

9. A method of quantitatively evaluating a braze bonding length of a specimen by using radiation, comprising:
   emitting radiation in a braze bonding length direction to each of a plurality of partial specimens which are obtained by cutting the specimen in a plane perpendicular to the braze bonding length direction;
   generating light of an amount corresponding to an intensity of transmissive radiation which is part of the emitted radiation, the part of the emitted radiation having passed through each of the partial specimens;
   photographing the light generated in accordance with the intensity of the transmissive radiation;
   calculating a braze bonding length of each of the partial specimens, from a light amount recognized from a photographed result obtained with respect to each of the partial specimens, based on a correlation between a braze bonding length and a light amount which is pre-acquired; and
   calculating the braze bonding length of the specimen by totaling the calculated braze bonding lengths of the respective partial specimens.

10. The method of claim 9, wherein the radiation is X rays.

11. The method of claim 9, wherein the specimen is a part of a mockup of an actual device, and the specimen is braze-bonded under the same condition as the actual device.

12. The method of claim 9, wherein the photographed result is a two-dimensional image, and each of the partial specimens includes an alignment portion for two-dimensional alignment of each of the partial specimens.

13. The method of claim 9, wherein the correlation is represented by a polynomial expression.

14. The method of claim 9, wherein each of the partial specimens is fixed such that the radiation is emitted to each of the partial specimens at an identical position.

15. The method of claim 9, wherein the light is generated by only the transmissive radiation.

16. The method of claim 9, wherein the generated light is photographed with respect to each of a plurality of frequency bands,
   the correlation is a pre-acquired correlation between the braze bonding length and the light amount with respect to each of the plurality of frequency bands, and
   when the braze bonding length of each of the partial specimens is calculated, the braze bonding length of each of the partial specimens is calculated, with respect to a frequency band that is any one of the plurality of frequency bands, from a light amount recognized from a photographed result at the frequency band, based on the correlation at the frequency band.

* * * * *